United States Patent
Shimase et al.

(10) Patent No.: US 7,027,935 B2
(45) Date of Patent: Apr. 11, 2006

(54) SAMPLE DISPENSING APPARATUS AND AUTOMATIC ANALYZER USING THE SAME

(75) Inventors: Akihiro Shimase, Hitachinaka (JP); Hiroyasu Uchida, Hitachinaka (JP); Katsuhiro Kambara, Hitachinaka (JP); Tomoyuki Tobita, Hitachinaka (JP)

(73) Assignee: Hitachi High Technologies Corp., Tokyo (JP)

( * ) Notice: Subject to any disclaimer, the term of this patent is extended or adjusted under 35 U.S.C. 154(b) by 0 days.

(21) Appl. No.: 10/634,775

(22) Filed: Aug. 6, 2003

(65) Prior Publication Data

US 2004/0034479 A1 Feb. 19, 2004

(30) Foreign Application Priority Data

Aug. 7, 2002 (JP) .............................. 2002-229374

(51) Int. Cl.
*G01F 1/00* (2006.01)
*G01F 7/00* (2006.01)

(52) U.S. Cl. ...................................................... 702/47

(58) Field of Classification Search .................. 702/45, 702/47, 50, 55, 64, 71, 81, 82, 98, 100, 138; 73/152.18, 708
See application file for complete search history.

(56) References Cited

U.S. PATENT DOCUMENTS 5,540,081 A * 7/1996 Takeda et al. .................. 73/37

| | | | |
|---|---|---|---|
| 6,022,747 A * | 2/2000 | Gherson et al. | ............... 436/69 |
| 2004/0057872 A1* | 3/2004 | Shibuya et al. | ............... 422/64 |

FOREIGN PATENT DOCUMENTS

| JP | 7-198726 | 8/1995 |
|---|---|---|
| JP | 11-83868 | 3/1999 |
| JP | 11-083868 | * 3/1999 |
| JP | 2000-39440 | 2/2000 |
| JP | 2002-333449 | * 11/2002 |

OTHER PUBLICATIONS

Japan Standard Association, Quality engineering application course, Technical development in MTS system, Jun. 20, 2002.

* cited by examiner

*Primary Examiner*—Michael Nghiem
(74) *Attorney, Agent, or Firm*—Mattingly, Stanger, Malur & Brundidge, P.C.

(57) ABSTRACT

A sample dispensing apparatus is realized which can detect a dispensing abnormality occurred during the sample dispensing operation regardless of the type and the extent of the abnormality. A pressure sensor is connected to a dispensing flow passage system, including a sample probe and a dispensing syringe, and a plurality of output values of the pressure sensor during the sample dispensing operation are taken in. A multi-item analysis (based on the Mahalanobis distance) is carried out by using, as items, the plurality of taken-in output values of the pressure sensor. Whether the dispensing is normally performed or not is determined by comparing an analysis result with a threshold. A highly reliable determination result is obtained in spite of variations of sensitivity of the pressure sensor.

17 Claims, 14 Drawing Sheets

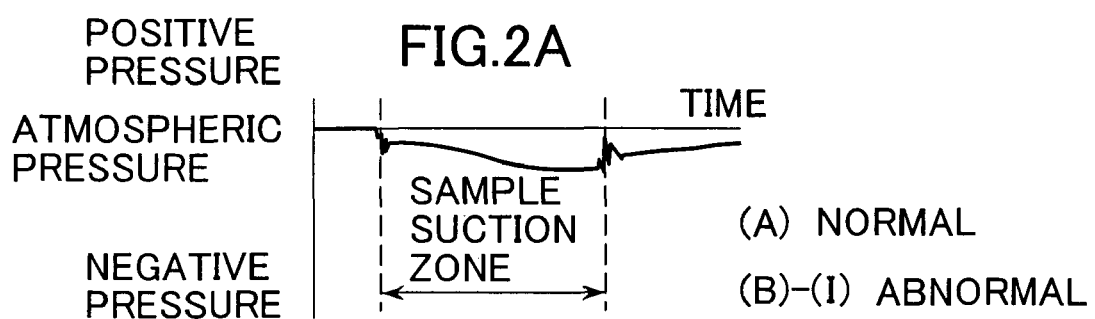
FIG.2A
POSITIVE PRESSURE
ATMOSPHERIC PRESSURE
NEGATIVE PRESSURE
TIME
SAMPLE SUCTION ZONE
(A) NORMAL
(B)–(I) ABNORMAL
FIG.2B
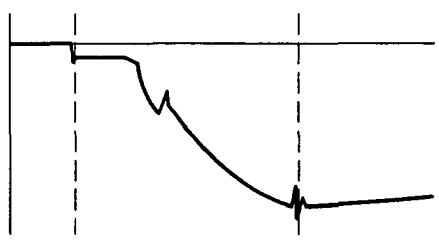
FIG.2C
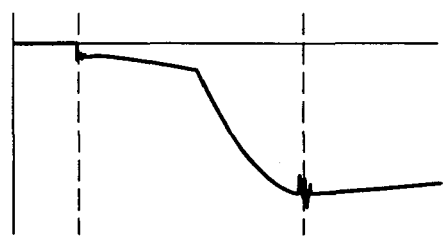
FIG.2D
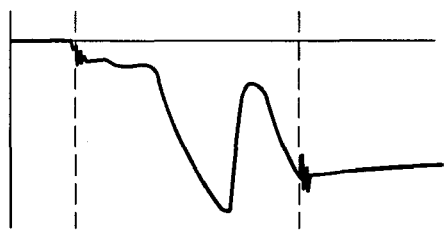
FIG.2E
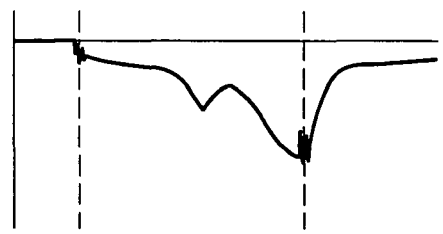
FIG.2F
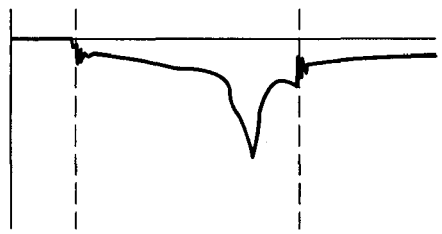
FIG.2G
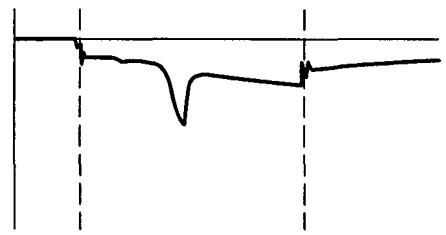
FIG.2H
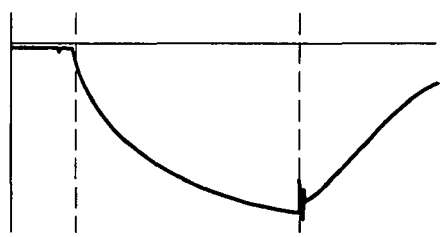
FIG.2I
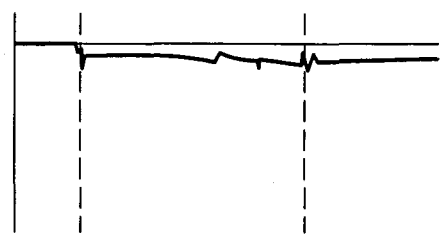

| ITEM NO. | 1 | 2 | ... | k-1 | k |
|---|---|---|---|---|---|
| PRESSURE VALUE | p1 | p2 | ... | pk-1 | pk |

FIG.6

| EVENT NO \ ITEM NO | 1 | 2 | ... | k-1 | k |
|---|---|---|---|---|---|
| 1 | p11 | p12 | ... | p1k-1 | p1k |
| 2 | p21 | p22 | ... | p2k-1 | p2k |
| ⋮ | ... | ... | ... | ... | ... |
| n-1 | pn-11 | pn-12 | ... | pn-1k-1 | pn-1k |
| n | pn1 | pn2 | ... | pnk-1 | pnk |

FIG.7

| PRESSURE WAVEFORM | MAHALANOBIS DISTANCE $D_2$ |
|---|---|
| (a) NORMAL | 1 |
| (b) | 1,185 |
| (c) | 2,442 |
| (d) | 4,176 |
| (e) | 814 |
| (f) | 1,225 |
| (g) | 179 |
| (h) | 603 |
| (i) | 36 |

FIG.8

| AVERAGE OF $D_2$ IN NORMAL DISPENSING (n=288) | 1.00 |
|---|---|
| STANDARD DEVIATION OF $D_2$ IN NORMAL DISPENSING (n=288) | 0.56 |

| PRESSURE WAVEFORM | −5kPa | +5kPa | ×0.5 | ×1.5 |
|---|---|---|---|---|
| (a) NORMAL | 7 | 6 | 7 | 6 |
| (b) | 1,158 | 1,225 | 227 | 2,902 |
| (c) | 2.510 | 2,387 | 551 | 5,699 |
| (d) | 4,141 | 4,224 | 1,031 | 9,463 |
| (e) | 856 | 785 | 204 | 1,858 |
| (f) | 1,183 | 1,280 | 286 | 2,844 |
| (g) | 187 | 184 | 56 | 397 |
| (h) | 614 | 604 | 164 | 1,343 |
| (i) | 53 | 32 | 24 | 64 |

SAMPLE DISPENSING APPARATUS AND AUTOMATIC ANALYZER USING THE SAME

BACKGROUND OF THE INVENTION

1. Field of the Invention

The present invention relates to a sample dispensing apparatus for dispensing a liquid sample, such as blood and urine, and an automatic analyzer using the sample dispensing apparatus. More particularly, the present invention relates to a sample dispensing apparatus with a function of enabling clogging of a suction/ejection nozzle to be detected with high accuracy, and an automatic analyzer using the sample dispensing apparatus.

2. Description of the Related Art

An automatic analyzer, such as a biochemical automatic analyzer or an immune automatic analyzer, includes a sample dispensing apparatus for automatically sucking and ejecting (hereinafter referred to as "dispensing") a liquid sample from a sample vessel from and into a reaction vessel.

Conventionally, the sample dispensing apparatus comprises a sample probe, a dispensing syringe connected to the sample probe, and a mechanism for moving the sample probe to a predetermined position. The sample dispensing apparatus repeats a dispensing operation as follows. A fore end of the sample probe is inserted in a sample, and the dispensing syringe is driven to move over a predetermined distance to suck a predetermined amount of sample. Then, the sample probe is moved to the reaction vessel into which the sucked sample is ejected.

In sample tests such as biochemical tests, blood serum and plasma are employed as samples in many cases. If these samples are left to stand for a long time from sampling to inspection, a solid (hereinafter referred to as a clot), e.g., fibrin, is generated in the sample. Then, if such a sample is put, as it is, in an automatic analyzer, the sample probe may clog with the generated clot. Upon the clogging of the sample probe, a predetermined amount of sample cannot be dispensed to the reaction vessel and an accurate analysis result can no longer be obtained. This results in a great loss of analysis reliability in the automatic analyzer.

To overcome the disadvantage described above, many proposals have been made with the concept of providing a pressure sensor in a dispensing flow passage including the sample probe, and detecting the clogging of the sample probe based on detected pressure fluctuations. Japanese Unexamined Patent Application Publication No. 7-198726 pays attention to a second derivative value of a waveform of the pressure fluctuations and states that abnormal suction can be detected by comparing the second derivative value with a threshold (hereinafter referred to as "first related art"). Also, Japanese Unexamined Patent Application Publication No. 11-83868 pays attention to a pressure remaining on the negative side after the end of the sucking operation and it compares the remaining pressure with a threshold to determine the occurrence of clogging when the remaining pressure is lower than the threshold (hereinafter referred to as "second related art"). Further, Japanese Unexamined Patent Application Publication No. 2000-39440 discloses a technique of comparing an area value, which is obtained by integrating an output of a pressure sensor, with a preset reference value and determining an abnormality in the sample dispensing operation (hereinafter referred to as "third related art").

SUMMARY OF THE INVENTION

The abnormal dispensing causing an analysis failure does not always occur only upon the above-described clogging of the sample probe. For example, in a sample dispensing apparatus for detecting a level of the sample surface from a change of an electrical variable, such as a resistance value or a capacitance, which occurs upon the sample probe contacting with the sample, when a sample having many bubbles in its surface is dispensed, it is determined that the sample probe has reached the sample surface, in spite of the sample probe being present in a bubble layer. In response to the determination, the operation of sucking the sample is performed to suck air instead of the sample (hereinafter referred to as "empty suction"). Also in this case, therefore, a certain amount of sample cannot be dispensed and an accurate analysis result can no longer be obtained.

Thus, there are a plurality of causes giving rise to the abnormal dispensing, and all waveforms of pressure fluctuations occurred in the abnormal dispensing are not the same and differ from each other. Accordingly, any related art has a problem that it can only detect a certain type of abnormality, and cannot detect another type of abnormality.

FIGS. 2A to 2I each show a waveform of pressure fluctuations resulting when a sample is sucked in a sample dispensing apparatus provided with a pressure sensor. In FIGS. 2A to 2I, the vertical axis represents a pressure and the horizontal axis represents a time. In the vertical axis, an upper side represents a positive pressure and a lower side represents a negative pressure with the atmospheric pressure being a reference.

FIG. 2A shows the waveform of the pressure fluctuations in the case of normal suction. In the normal sucking operation, the pressure starts to lower at the same time as the start of the suction and then moderately changes during a sample suction zone. Such a moderate change during the sample suction zone depends on sample properties, such as viscosity and density, and the suction speed, i.e., the driving speed of the dispensing syringe. At the end of the suction, the pressure largely deflected to the negative pressure side returns toward the atmospheric pressure reference.

FIGS. 2B, 2C and 2D each show the case in which the sample probe is clogged with a clot during the sample suction and the sample probe is brought into a completely blocked state (hereinafter referred to as "complete clogging". In this case, the amount of sample which should have been sucked after the clogging is lost and an accurate analysis result cannot be obtained. Looking at the waveform of the pressure fluctuations, the pressure lowers to a large extent at the same time as the occurrence of clogging, and does not restore even after the end of the sample suction. Thus, in the case of complete clogging, the waveform of the pressure fluctuations apparently exhibits different features from those in the case of normal suction both during and after the sample suction, and therefore abnormal suction can be reliably detected with the related art.

FIGS. 2E, 2F and 2G each show the waveform of the pressure fluctuations resulting when a clot is sucked. More specifically, the clot size is not so large as to completely clog the sample probe and is smaller than the diameter of an opening of the sample probe to such an extent that the clot is sucked into the sample probe (hereinafter referred to as "small clot suction". If a small clot is present in the dispensed sample, the amount of the sucked sample is lost correspondingly, and there is a risk that the clot may adversely affect the analysis. For that reason, the small clot suction is also categorized into abnormal dispensing. In general, the sample probe is of a structure that the probe opening has the smallest diameter. The small clot undergoes resistance when passing through the probe opening and causes a disturbance in the waveform of the pressure fluctuations. Subsequently, when the sucked small clot reaches, for example, an inner space of the sample probe of which diameter is larger than the opening diameter, the disturbance in the waveform of the pressure fluctuations is settled. In such a case, because the pressure after the suction is restored to a level comparable to that in the normal suction, the abnormal suction cannot be detected by the second related art wherein attention is paid to the pressure remaining on the negative side after the end of the sucking operation. Also, when employing the third related art wherein the sensor output is integrated, it is very difficult to detect the cases of FIGS. 2F and 2G in each of which an area of region showing a pressure disturbance is small. To detect that type of abnormal suction, a threshold used for determining the normal range must be more closely set. However, this solution increases a possibility that the normal suction is falsely detected as the abnormal suction.

FIG. 2H shows the waveform of the pressure fluctuations in the case of sucking a highly viscous sample (hereinafter referred to as "highly viscous sample suction"). As compared with the waveform of the pressure fluctuations in the case of normal dispensing, a larger negative pressure appears in the sample suction zone, and the pressure after the end of the sucking operation returns toward the atmospheric pressure reference at a later timing. Accordingly, the sample probe is withdrawn from the sample surface before the pressure is not sufficiently restored, and a certain amount of sample is left without being sucked. This also results in abnormal dispensing. The pressure fluctuations in this case exhibit a large negative pressure, but change moderately. Such pressure fluctuations cannot hence be detected by the first related art wherein an abrupt pressure change is detected by utilizing differentiation (second derivative value).

FIG. 2I shows the waveform of the pressure fluctuations in the case of empty suction. As compared with the waveform of the pressure fluctuations in the case of normal dispensing, the pressure is hardly deflected to the negative side. It is also difficult to this type of abnormal suction with the first related art because there occurs no abrupt pressure change, similarly to the case of highly viscous sample suction. Further, because the negative pressure does not remain after the end of the sucking operation, this type of abnormal suction cannot be detected with the second related art as well. Incidentally, the empty suction may be caused by not only false detection of arrival of the sample probe to the sample surface as described above, but also by missed placement of the sample or an insufficient amount of sample.

As described above, there are plural kinds of abnormal dispensing, and the pressure fluctuations occur in different waveforms from each other. This has resulted in the problem that each related art can only deal with a particular type of abnormality, i.e., it cannot deal with various types of abnormality.

A first object of the present invention is to detect all types of abnormal dispensing causing analysis failures, including the complete clogging, the small clot suction, the highly viscous sample suction, and the empty suction, regardless of the type and the extent of abnormality.

When detecting an abnormality by sensing the pressure fluctuations as described above, it is a major problem how to deal with variations of the pressure value. The variations of the pressure value are caused by variations of a pressure measuring system and variations of a pressure measured system, as well as by errors due to variations of viscosity of the dispensed sample and an influence of external environment.

The variations of the pressure measuring system include, for example, variations of sensitivity of the pressure sensor and variations of components of an amplification circuit for amplifying an output signal of the pressure sensor. Ideally, when the same pressure is measured, the same output value is to be obtained. In practice, however, exactly the same output value is not always resulted due to the above-mentioned variations. Also, even when the same dispensing operation is performed using the same pressure measuring system, the pressure itself may vary with variations of the pressure measured system, e.g., variations of the inner diameter of the sample probe and variations of the length of a dispensing flow passage.

If those various types of variations cannot be dealt with, even the normal dispensing is falsely detected to be abnormal or conversely the abnormal dispensing is missed at an increased rate, thus resulting in a noticeable reduction of the detection ability. Hitherto, those various types of variations have been overcome by a method comprising the steps of assembling an adjusting device in the amplification circuit, measuring a reference pressure and precisely adjusting an output value to be kept the same, or by a method of narrowing working tolerances of the sample probe and a pipe of the dispensing flow passage. However, implementing the step(s) of such a method raises a problem of pushing up a cost.

Furthermore, because errors due to variations of viscosity of the dispensed sample and influences of external environment are uncontrollable factors, those errors must be dealt with by reducing the detection ability.

A second object of the present invention is to accurately detect an abnormality of dispensing without reducing the detection ability with no need of performing close adjustment or narrowing working tolerances.

In the event of abnormal dispensing, subsequent operations for dealing with the abnormal dispensing is desirably processed in an automatic manner. For example, when the sample probe is clogged with a clot, it is desired that operations of washing the sample probe and confirming whether the clogging is removed be automatically performed. Particularly, if the removal of the clogging is not reliably confirmed, the amount of sample dispensed after the removal cannot be regarded as reliable. As a technique of confirming the removal of the clogging, it is also proposed to check a pressure value after the washing (Japanese Unexamined Patent Application Publication No. 6-109745). In this technique, however, variations of the pressure value also cause a problem as described above. A technique capable of reliably confirming the removal of the clogging is therefore demanded. Accordingly, a third object of the present invention is to provide a system for carrying out operations subsequent to the abnormal dispensing without reducing the analysis processing ability and the analysis reliability, including reliable confirmation of the removal of the clogging.

To achieve the above first and second objects, a sample dispensing apparatus is constructed as follows.

In a sample dispensing apparatus comprising a probe for sucking and ejecting a sample, a dispensing syringe for generating a pressure in the probe to suck and eject the sample, a dispensing flow passage connecting the probe and the dispensing syringe, and a control unit for controlling sucking and ejection operations of the sample, the apparatus further comprises at least one pressure sensor for detecting a pressure in the dispensing flow passage; a pressure value storing unit for time-serially storing output values of the pressure sensor during an operation of dispensing the sample; a storage unit for storing a reference database consisted of time-serial output values of the pressure sensor, which are obtained when the sample is normally sucked or ejected by the probe; and a determining unit for carrying out multi-variable analysis of both the reference database and comparison data created based on the output values of the pressure sensor time-serially stored in the pressure value storing unit, and for determining the presence or absence of an abnormality in the dispensing operation of the sample based on an analysis result.

The above-mentioned multi-variable analysis can be typically carried out by a method using the Mahalanobis distance (called MTS: Mahalanobis & Taguchi System), or a method using a neural network. However, any other method is also applicable so long as it can perform the multi-variable analysis executing comparison in consideration of not only the magnitude of an item value itself, but also the correlation between items. The MTS method is a method used in a multi-variable analysis which is applied in a various field, and described in detail, for example, in "Japan Standard Association, Quality engineering application course, Technical development in MTS system, Jun. 20, 2002".

Also, to achieve the above third object, the apparatus and its functions are constituted as follows.

In the sample dispensing apparatus, the apparatus further comprises a discriminating unit for, when the abnormality of sample dispensing is detected, comparing a pressure value immediately before the end of the sample sucking operation with a preset threshold, and for discriminating one of plural causes of the dispensing abnormality.

Also, the sample dispensing apparatus makes a determination as to an abnormality of dispensing when a fluid having a known physical property, such as viscosity and density, is dispensed as a sample, thereby determining the presence or absence of an abnormality in the dispensing function of the sample dispensing apparatus.

Further, the sample dispensing apparatus has a function of, when the abnormality of sample dispensing is detected in a cleaning unit for cleaning the interior of the dispending flow passage, including the sample probe, and in the sample dispensing apparatus, washing the interior of the dispensing flow passage including the sample probe, then dispensing a fluid having a known physical property, such as viscosity and density, and determining the dispensing abnormality in the fluid dispensing, thereby determining whether the dispensing function of the sample dispensing apparatus is restored. Further, in the sample dispensing apparatus, the dispensing operation is stopped when the abnormality of sample dispensing is detected and thereafter the dispensing function of the sample dispensing apparatus is not restored even after repeating the washing a predetermined number of times.

In an automatic analyzer comprises the sample dispensing apparatus, a cleaning tank for washing the interior of the dispensing flow passage, including a sample probe, and an outer surface of the sample probe, a reaction vessel cleaning mechanism, and a reaction vessel repeatedly used after being washed by the reaction vessel cleaning mechanism, when an abnormality of dispensing is detected during suction of a sample, the sample is discarded into the cleaning tank without ejecting the sample into the reaction vessel.

Also, in the automatic analyzer including the sample dispensing apparatus, when the abnormality of sample dispensing is detected, a cause of the dispensing abnormality is found out from among a plurality of classified causes and a counteraction corresponding to the cause is performed.

Further, in the automatic analyzer including the sample dispensing apparatus, when the abnormality of sample dispensing is detected, the relevant sample is repeatedly dispensing within a predetermined number of times. Moreover, in the automatic analyzer including the sample dispensing apparatus, when the dispensing abnormality still continues even after repeatedly dispensing the relevant sample within the predetermined number of times, the dispensing of the relevant sample is canceled and dispensing of a next sample is started.

According to the present invention, since various types of abnormal dispensing causing analysis failures can be all detected regardless of the type and extent of abnormality, reliability of the sample dispensing apparatus and analysis results of the automatic analyzer employing the sample dispensing apparatus can be increased. Consequently, the present invention is also effective in reducing labor and cost required for management of samples in an inspection room.

Further, the method of determining an abnormality of dispensing according to the present invention has sufficient robustness against variations of sensitivity of the pressure sensor, and is able to accurately detect the abnormality of dispensing without reducing the detection ability with no need of performing close adjustment or narrowing working tolerances. As a result, it is possible to suppress the cost that is otherwise expected to increase due to the necessity of those additional steps.

In addition, according to the present invention, when there occurs a dispensing abnormality, the subsequent actions for dealing with the abnormality can be automatically performed, and therefore the processing efficiency can be increased. Also, in the event of an abnormality, whether the abnormality has been removed can be detected with high accuracy, and hence higher reliability is ensured.

BRIEF DESCRIPTION OF THE DRAWINGS

FIGS. 2A to 2I are time charts showing waveforms of pressure fluctuations occurred in a dispensing flow passage during sample suction;

FIG. 6 is a table showing a reference space in the present invention;

FIG. 7 is a table showing results obtained by calculating the Mahalanobis distance in the present invention for each of the waveforms of the pressure fluctuations shown in FIGS. 2A to 2I;

FIG. 8 is a table showing an average and a standard deviation of the Mahalanobis distances calculated in the present invention based on the waveform of the pressure fluctuations resulting when normal dispensing is performed;

DESCRIPTION OF THE PREFERRED EMBODIMENTS

An embodiment of the present invention will be described below with reference to the drawings.

Figure 1:
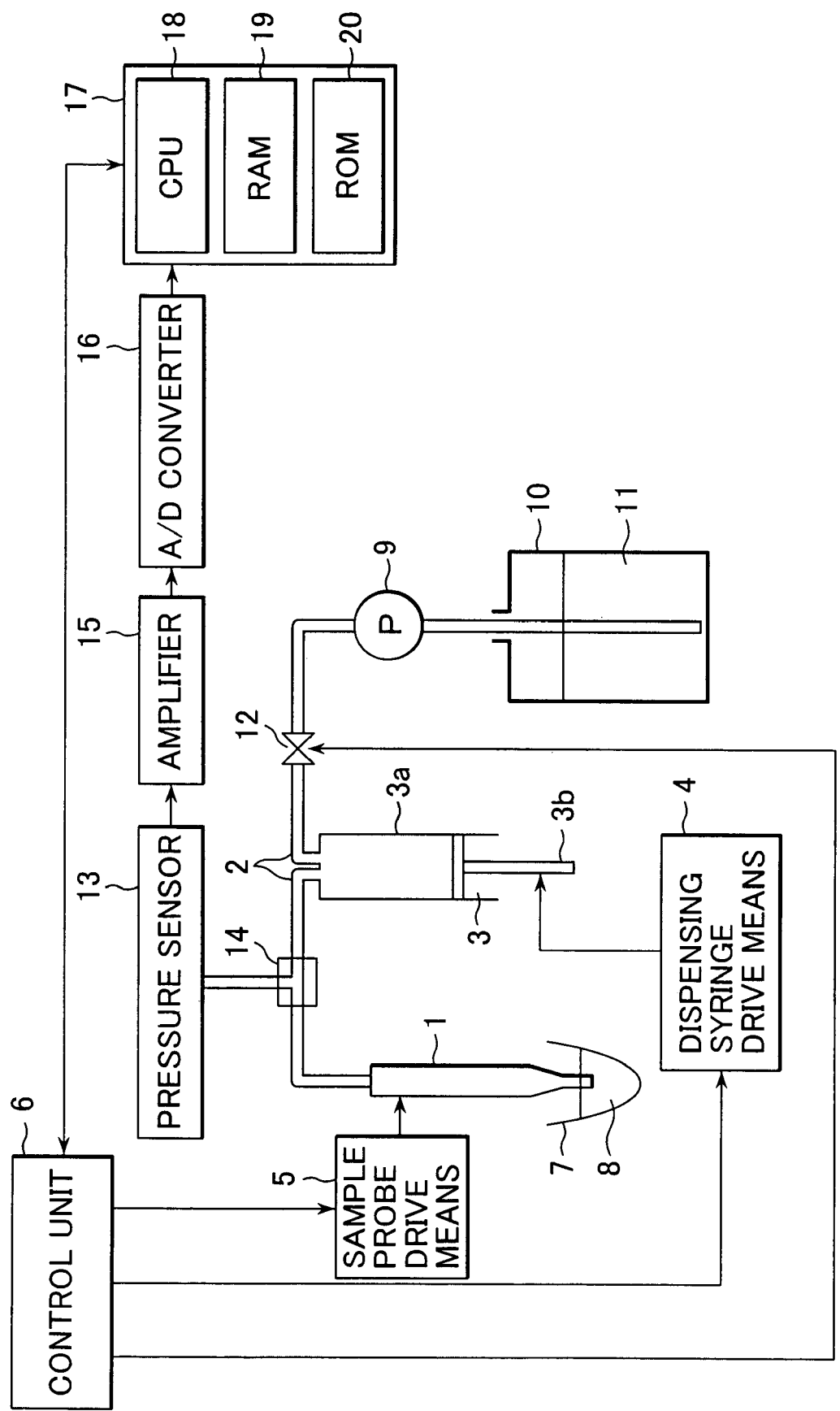
FIG. 1 is a block diagram of a sample dispensing apparatus according to the present invention.

FIG. 1 is a block diagram of a sample dispensing apparatus according to the present invention.

A sample probe 1 is connected to a dispensing syringe 3 through a tube 2, and the interiors of these components are filled with a liquid. The dispensing syringe 3 comprises a cylinder 3a and a plunger 3b. A dispensing syringe drive means 4 is connected to the plunger 3b. The cylinder 3a is held stationary, and the plunger 3b is driven by the dispensing syringe drive means 4 to move up and down so that a sample is dispensed. Also, a sample probe drive means 5 is connected to the sample probe 1 and moves the sample probe 1 to a predetermined position. The dispensing syringe drive means 4 and the sample probe drive means 5 are each controlled by a control unit 6.

When the sample probe drive means 5 moves the sample probe 1 downward and the sample probe 1 enters a liquid sample 8 in a sample vessel 7, the dispensing syringe drive means 4 is driven to start the sucking operation of the dispensing syringe 3. It is here assumed that, before the sample probe 1 enters the liquid sample 8, air (segmenting air) is sucked in advance to prevent the sample 8 from mixing with the liquid filled in the sample probe 1. When the sample sucking operation is completed, the sample probe 1 is moved to a sample ejection position at which the dispensing syringe 3 performs the ejecting operation.

After the end of the dispensing operation, cleaning water 11 in a water supply tank 10 is sucked by a water supply pump 9 to flow under high pressure so that the sample probe 1 can be washed. The flow of the cleaning water is switched over by a solenoid valve 12 that is controlled by the control unit 6.

A pressure sensor 13, which is a means for detecting the abnormal dispensing in accordance with the main object of the present invention, is connected through a branching block 14 to a dispensing flow passage system including the sample probe 1, the tube 2, and the dispensing syringe 3. For the purpose of detecting pressure fluctuations in an opening of the sample probe 1 with high sensitivity, it is desired that the pressure sensor 13 be connected to the dispensing flow passage system at a position as close as possible to the sample probe 1.

An output signal of the pressure sensor 13 is amplified by an amplifier 15 and converted into a digital signal by an A/D converter 16. An output of the A/D converter 16 is sent to a microcomputer 17 in which an input signal is processed, as described later, to determine whether the dispensing is normally performed.

Figure 3:
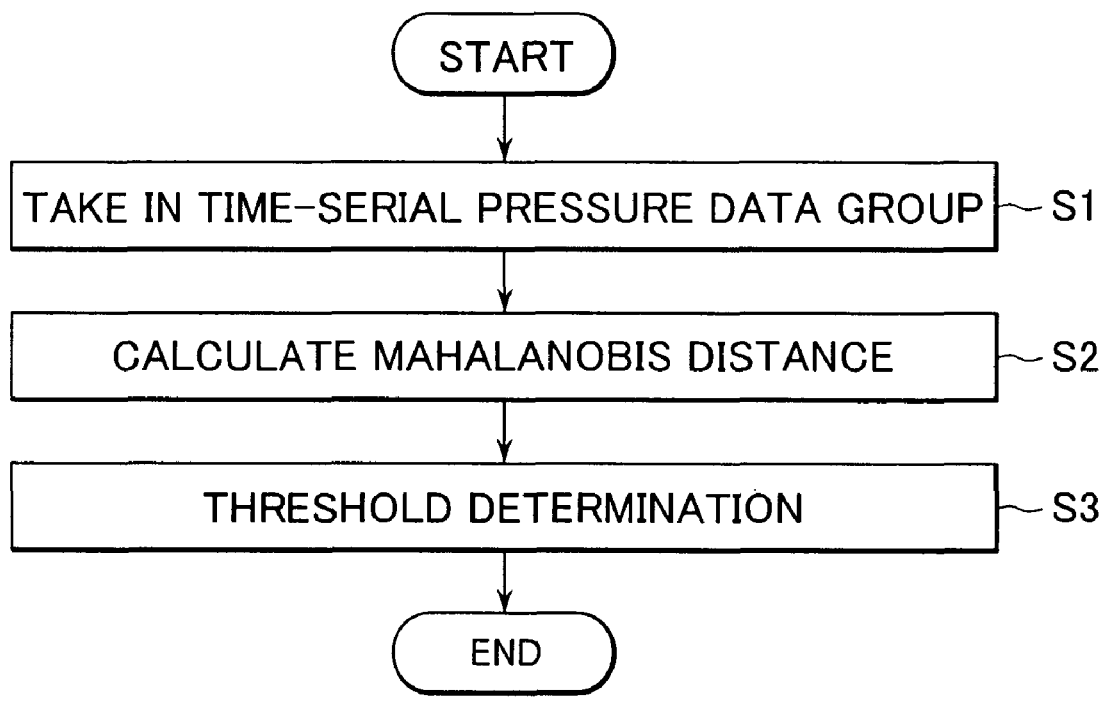
FIG. 3 is a control flowchart for detection of abnormal dispensing in the present invention.

FIG. 3 is a control flowchart for detection of abnormal dispensing in the present invention.

The internal pressure of the dispensing flow passage system, including the sample probe, during the sample dispensing always changes, including small changes, and the output of the pressure sensor also changes in a following way. In the present invention, a pressure value changing from moment to moment is time-serially taken in, and a set of taken-in pressure values (hereinafter referred to as a "group of time-serial pressure data") are employed as they are (S1). In the related art, attention is paid to only one time point, i.e., only one of the time-serial pressure values changing from moment to moment, or the changing pressure value is integrated or differentiated for conversion into a value in another dimension. An amount of information is therefore lost more or less. In the present invention, such a loss of information is avoided and the determination can be made with higher accuracy.

Next, the Mahalanobis distance is calculated from the group of time-serial pressure data obtained in the above step (S2). The Mahalanobis distance is one method of multi-variable analysis, and represents a scale for measuring whether a sample under inspection belongs to a reference group (hereinafter referred to as a "reference space"). In the present invention, a group of time-serial pressure data obtained in the normal dispensing operation serves as a reference, and this group is employed as the reference space.

The Mahalanobis distance takes a value near 1 when the dispensing is normally performed, whereas the Mahalanobis distance takes a value much larger than 1 when the dispensing is abnormal. By utilizing such a tendency, whether the dispensing is normal or abnormal is determined based on threshold determination (S3).

A method of taking in the group of time-serial pressure data and a method of calculating the Mahalanobis distance will be described in detail below.

Figures 4, 5:
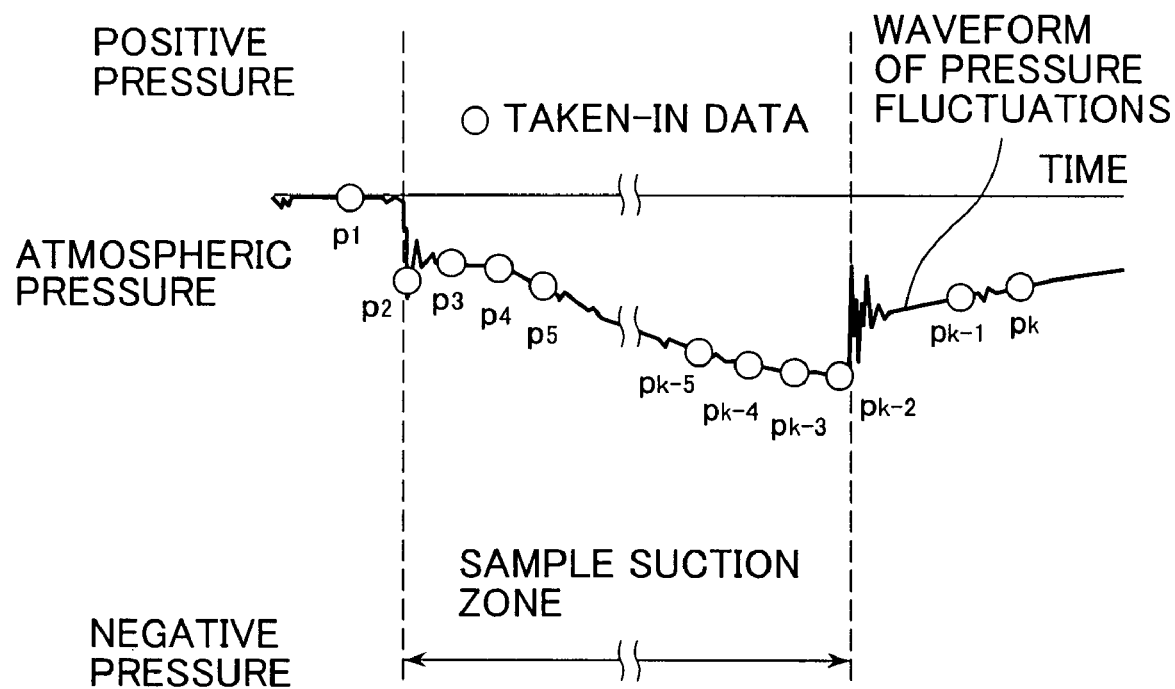
FIG. 4 is a time chart showing a method of taking in a group of time-serial pressure data in the present invention.
FIG. 5 is a table showing the group of time-serial pressure data in the present invention.

FIG. 4 shows the method of taking in the group of time-serial pressure data. As shown in FIG. 4, pressure values at k points are taken in from the waveform of pressure fluctuations changing from moment to moment.

Because an abnormality of the dispensing begins with an abnormality of the suction, the group of time-serial pressure data is taken in from a region with the sample suction zone being at the center. It is confirmed that the abnormality can be detected with high accuracy by using the group of time-serial pressure data belonging only to the sample suction zone, but the accuracy is further improved by adding pressure values at several points before and after the sample suction zone. Further, because a sign of the dispensing abnormality appears as a disturbance of the pressure fluctuations in the sample suction zone in many cases, the pressure fluctuations in the sample suction zone may also be taken in.

An interval at which the group of time-serial pressure data is to be taken in may be constant or variable. In other words, the sampling interval is not always required to be constant. Specifically, the sampling interval may be narrowed in a region where the abnormality of dispensing is apt to occur, or conversely it is widened in a region where the abnormality of dispensing hardly occurs, thus causing data to be taken in at a rough density.

It is however desired that, because the position at which the suction abnormality occurs in the sample suction zone is unknown, the pressure value be taken in at a constant interval during the sample suction zone. If the sampling interval is too wide, an abnormality occurred between adjacent sampling points corresponding to the interval would be missed. Conversely, if the sampling interval is too narrow and the number of taken-in data is increased, a later-described process of calculating the Mahalanobis distance would take a longer time. For those reasons, the sampling interval is desirably widened within the range in which the abnormality of dispensing can be detected. As a guideline, assuming that a region from a point at which the pressure starts to disturb due to the abnormality of dispensing to a point at which the disturbance is settled is called a pressure abnormal zone, the sampling interval can be set to ½ of the shortest pressure abnormal zone.

A method of taking in the group of time-serial pressure data at the k points can be performed by a manner of designating a sampling time at each point in advance and obtaining data only at the k points, or by a manner of initially taking in data at intervals as narrow as possible and thinning out the taken-in data to leave data only at the k points.

The group of time-serial pressure data thus obtained is put together as shown in FIG. 5. The pressure values at the respective points of time in FIG. 5 are utilized as items when calculating the Mahalanobis distance.

By carrying out the above-described processing on the data taken in from the normal dispensing, the group of time-serial pressure data can be obtained as a reference. FIG. 6 shows the groups of time-serial pressure data obtained by performing the normal dispensing n times. Thus, these groups constitute a reference space of n events and k items.

The term "normal dispensing" means that a normal sample is dispensed in a state in which normal dispensing is sufficiently feasible. The term "normal sample" means a sample which has viscosity in the viscosity range of samples handled by the sample dispensing apparatus and which contains no solid foreign matters, etc. The normal sample employed in, for example, the sample dispensing apparatus for use in a biochemical automatic analyzer for blood is a sample which has viscosity comparable to that of human serum and which contains no clots, etc. Further, the term "state in which normal dispensing is feasible" means a state in which variations of components of the sample dispensing apparatus, such as variations of the inner diameter of the sample probe and variations of sensitivity of the pressure sensor, fall within a predetermined tolerance regardless of possible causes, such as individual differences in manufacture between the components, influences of external environment, and deterioration over time, and the sample dispensing apparatus can sufficiently develop its own function without causing an abnormality, e.g., clogging of the sample probe.

When creating the reference space, it must be taken into consideration that, because the collected data is not merely statistic data and is statistic data obtained by collecting data in the normal dispensing, abnormal data must be excluded. However, if the above-mentioned variations, such as the variations of the sample viscosity and the variations of sensitivity of the pressure sensor, fall within the normal range, it is desirable to obtain data by positively dispersing the variations as far as within the normal range. This is effective in increasing the accuracy in the abnormality detection.

The number n of events contained in the reference space is preferably larger for the purpose of increasing the accuracy in the abnormality detection. However, if the number n of events is increased more than a necessary value, the economic cost would increase to a level not offset by the obtained information. Therefore, it is advantageous to determine the number n of events in consideration of the detection accuracy and the economic cost. With this regard, the number n of events must be larger than the number of items k because a correlation matrix described later cannot be determined if n is smaller k.

The use of the groups of time-serial pressure data and reference space, obtained as described above, is not limited to the case of dispensing the sample in a predetermined amount. When the amount of the dispensed sample changes regardless of increase or decrease, the sample is dispensed in accordance with a dispensing speed and a drive sequence of the dispensing syringe and the sample probe (hereinafter referred to as a "dispensing sequence"), which are optimum for the dispensing of the sample in a resulting amount, and the waveform of pressure fluctuations is also changed correspondingly. Therefore, the number of the groups of time-serial pressure data to be taken in and the method of taking in the groups of time-serial pressure data are changed for each amount of the dispensed sample, and the reference space is also prepared for each amount of the dispensed sample. Generally, maximum and minimum amounts of the dispensed sample and resolution of the dispensing are decided depending on specifications of a sample dispensing apparatus, and the number of different amounts of the dispensed sample is finite. Therefore, the groups of time-serial pressure data and the reference spaces are required just in that finite number.

Next, a description is made of a method of calculating the Mahalanobis distance from the groups of time-serial pressure data and the reference space both obtained as described above.

After repeating the sampling of each of the groups $p_1$, $p_2, \ldots, p_k$ of time-serial pressure data, shown in FIG. 5, n times, an average is calculated for each item from the reference space of n events and k items shown in FIG. 6 as follows:

$$\bar{p}_1, \bar{p}_2, \ldots, \bar{p}_k$$

Also, standard deviations $\sigma_1, \sigma_2, \ldots, \sigma_k$ are calculated for each of the items. Then, normalization is made based on calculation expressed by a formula (1) given below:

[Equation 1]

$$p_i = \frac{p_i - \bar{p}_i}{\sigma_i} (\text{where } i = 1, 2, \ldots, k) \qquad (1)$$

On the other hand, the reference space is expressed as a matrix of n columns and k rows, and a matrix A of k×k is derived by obtaining a correlation matrix of the matrix of n columns and k rows. Assuming an inversed matrix of the matrix A to be $A^{-1}$, the Mahalanobis distance $D^2$ can be expressed by a formula (2) given below:

[Equation 2]

$$D^2 = \frac{1}{k}(p_1 \ldots p_k)A^{-1}\begin{pmatrix} p_1 \\ \vdots \\ p_k \end{pmatrix} \qquad (2)$$

Of those calculations, the average and the standard deviation for each item of the reference space and the inversed matrix of the correlation matrix in the reference space may be calculated in advance, and the calculated results may be prepared as parameters beforehand. This is advantageous in omitting the effort of carrying out the calculations and simplifying the calculation process when repeatedly calculating the Mahalanobis distance.

The processes described above will be described below in connection with the sample dispensing apparatus shown in FIG. 1.

When dispensing of some sample is requested on the sample dispensing apparatus, the control unit 6 sends control commands to the dispensing syringe drive means 4 and the sample probe drive means 5. At the same time, instructions from the control unit 6 are also sent to the microcomputer 17 to make effective the function of detecting the abnormality of dispensing.

When the sample dispensing starts, the microcomputer 17 takes in the group of time-serial pressure data and stores the taken-in data in a RAM 19. The method of taking in the data is selected as one optimum for the amount of sample dispensed at that time. After the end of taking-in of the groups of time-serial pressure data, a CPU 18 calculates the Mahalanobis distance based on the above formulae (1) and (2). The parameters required for the calculations, i.e., the average and the standard deviation for each item of the reference space and the inversed matrix of the correlation matrix in the reference space have been calculated for each of all available amounts of the dispensed sample and stored in a ROM 20 beforehand. Therefore, the parameters in match with the amount of sample dispensed at that time are selected. After calculating the Mahalanobis distance, threshold determination is performed based on the calculated value. The threshold is not required to be prepared as a different value for each of the amounts of the dispensed sample, and it is just required to be set to one value. The reason resides in that the Mahalanobis distance is an index indicating whether a target is equal to or different from a reference waveform, and the reference waveform is prepared separately for each of the amounts of the dispensed sample. A result of the threshold determination is returned to the control unit 6, and based on the determination result, the control unit 6 makes determination in the subsequent process.

According to the above-described method used in the present invention, the Mahalanobis distance is calculated for each of various practical waveforms of pressure fluctuations as follows.

FIG. 7 shows results obtained by calculating the Mahalanobis distance for each of the waveforms of the pressure fluctuations shown in FIGS. 2A to 2I. Also, FIG. 8 shows an average and a standard deviation of the Mahalanobis distances similarly calculated with the sampling number n set to 288 (n=288) based on the waveform of the pressure fluctuations resulting when the normal dispensing is performed.

As seen from the results shown in FIGS. 7 and 8, a significant difference appears in the Mahalanobis distance between the case of normal dispensing shown in FIG. 2A and each of the cases of abnormal dispensing shown in FIGS. 2B to 2I, and therefore the above-mentioned types of abnormal dispensing can be all detected.

Next, a description is made of that the function of detecting the abnormality of dispensing according to the present invention has high robustness and the determination result is not so affected even with the presence of, e.g., individual differences between pressure sensors.

Figure 9A:
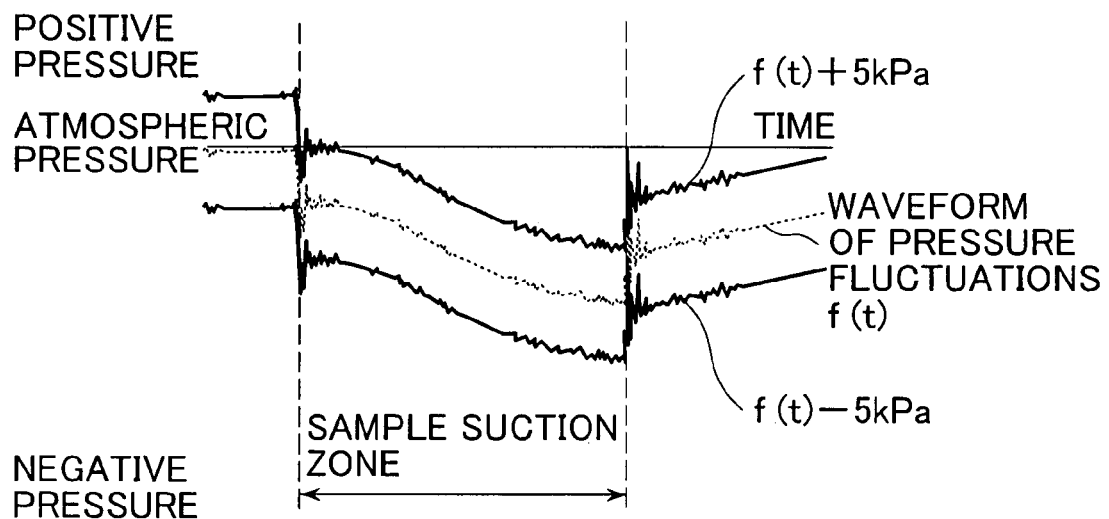
FIGS. 9A and 9B are each a time chart resulting from waveform processing carried out on the waveform of the pressure fluctuations in the normal dispensing.
Figure 9B:
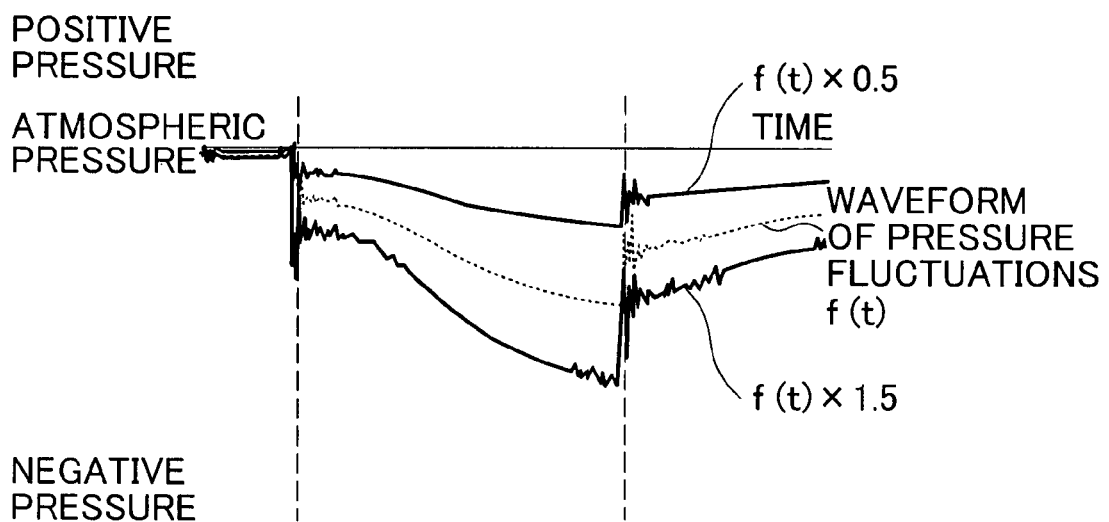
Figures 10, 11:
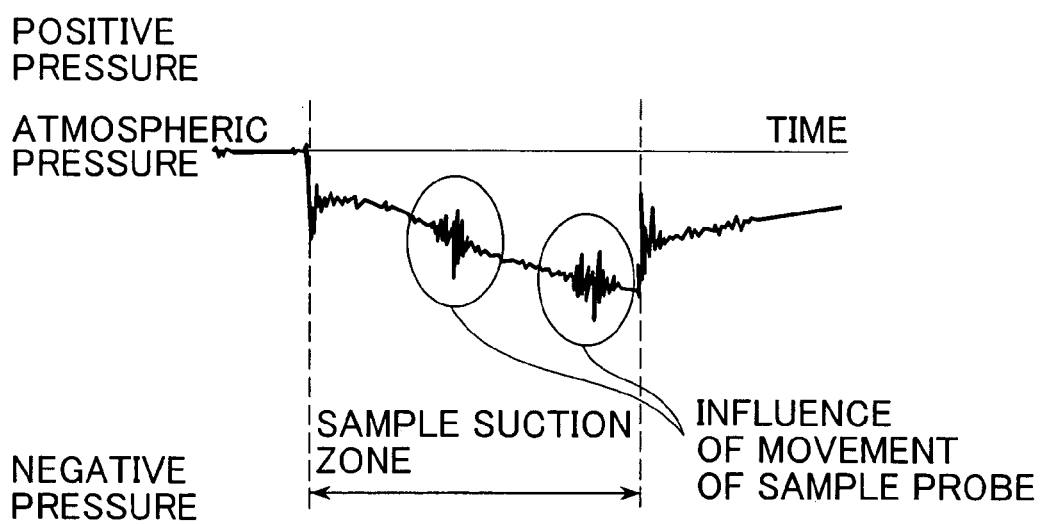
FIG. 10 is a table showing results obtained by carrying out waveform processing on each of the waveforms of the pressure fluctuations shown in FIGS. 2A to 2I and then calculating the Mahalanobis distances in the present invention.
FIG. 11 is a time chart showing a waveform of pressure fluctuations obtained when dispensing a sample in accordance with a certain dispensing sequence.

FIG. 9A shows waveforms of pressure fluctuations resulting from shifting the original waveform by 5 kPa in each of the positive and negative sides of the vertical axis on an assumption that the output of the pressure sensor is susceptible to offset. Also, FIG. 9B shows waveforms of pressure fluctuations resulting from multiplying the original waveform by 0.5 and 1.5 in the direction of the vertical axis on an assumption that the gain of the pressure sensor varies. FIG. 10 shows results obtained by carrying out similar waveform processing carried out on the each of the waveforms of the pressure fluctuations shown in FIGS. 2A to 2I and then calculating the Mahalanobis distances for each waveform.

While in the case of normal dispensing the Mahalanobis distance usually takes a value near 1, it may take a value larger than 1 even in the normal case shown in FIG. 2A with the waveform processing described above. However, there still exists a significant difference in the Mahalanobis distance from a value calculated in the case of abnormal dispensing, and hence discrimination can be satisfactorily made between the normal and abnormal cases.

The reason why those results can be obtained is that the method used in the present invention compares the measured value with the reference in consideration of not only the magnitude of an item value itself, but also the correlation between items. When the waveform of the pressure fluctuations is disturbed to a large extent as shown in FIG. 2B, for example, such a disturbance is apparently detected to be abnormal because not only item values in a disturbing region, but also the correlation between items differ from those resulting from the reference waveform. On the other hand, when the output offset and gain variations of the pressure sensor occur as shown in FIGS. 9A and 9B, the item values are deviated from the reference values, but the correlation between items is held substantially the same. As a result, such a case is detected to be normal based on overall determination.

The related art is not robust against the output offset and gain variations of the pressure sensor shown in FIGS. 9A and 9B because the determination is made based on only a value still belonging to the pressure dimension in any of the case of using a value extracted from a part of the waveform of the pressure fluctuations and the case of using a value resulting from integration or differentiation. To avoid such a drawback in the related art, the output offset and gain of the pressure sensor must be adjusted at a considerable cost, or the detection ability must be reduced by moderating the threshold reference.

Further, the present invention can effectively deal with the case in which the waveform of the pressure fluctuations is regularly disturbed.

FIG. 11 shows a waveform of pressure fluctuations obtained when dispensing a sample in accordance with a certain dispensing sequence. In the waveform of FIG. 11, pulsations different from ordinary pressure fluctuations appear twice during the sample suction zone. The dispensing sequence used in this case lowers the sample probe twice; namely, it comprises the steps of lowering the sample probe as a first stroke to a level below the sample surface, and then lowering the sample probe twice to avoid the empty suction that will otherwise occur as a result of a descent of the sample surface due to the sample suction. Since the sample probe is connected to the pressure sensor through the tube, etc., the liquid in the dispensing flow passage, including the sample probe, vibrates with movement of the sample probe, and the vibration is transmitted to the pressure sensor. Also, the pressure sensor may pick up other kinds of vibrations depending on how the pressure sensor is fixed.

Such a disturbance of the waveform of the pressure fluctuations is unavoidably caused depending on the dispensing sequence, and it can be regarded as a regular disturbance caused in the same positions each time the sample is dispensed in accordance with the same sequence. Therefore, that disturbance is not an abnormal sign and must not be falsely detected as being abnormal.

In the present invention, when preparing the reference space, the disturbance such as shown in FIG. 11 appears as a larger variation of the item value (pressure value) taken in the region where the disturbance has occurred. This means that the standard deviation of the relevant value increases and, looking from the viewpoint of the above-mentioned formula (1), a weighting factor for the relevant item is reduced correspondingly. Therefore, the calculated result of the Mahalanobis distance is not so affected even with a disturbance of the value of the relevant item. The present invention can satisfactorily deal with a regular disturbance of the pressure fluctuations because of considering the point of time at which the disturbance occurs and the information regarding the extent of disturbance.

When a pressure disturbance having high frequency occurs as shown in FIG. 11, removal of the disturbance is expected by carrying out signal processing to remove a high frequency component. Also, when the output offset of the pressure sensor occurs as shown in FIG. 9A, the output offset can be ignored by carrying out signal processing to calculate the difference from an initially taken-in pressure value. With the technique of the present invention, highly accurate results are obtained in spite of that those types of signal processing are not carried out on the original output of the pressure sensor. While that is one advantage of the present invention, i.e., simplification of processing, the technique of the present invention can also be applied to data obtained after those types of signal processing. If those types of signal processing are able to increase the detection accuracy and will not raise a problem in terms of processing time, the data processed in that way should be positively employed. Such a modification is also involved in the purport of the present invention.

Figure 12:
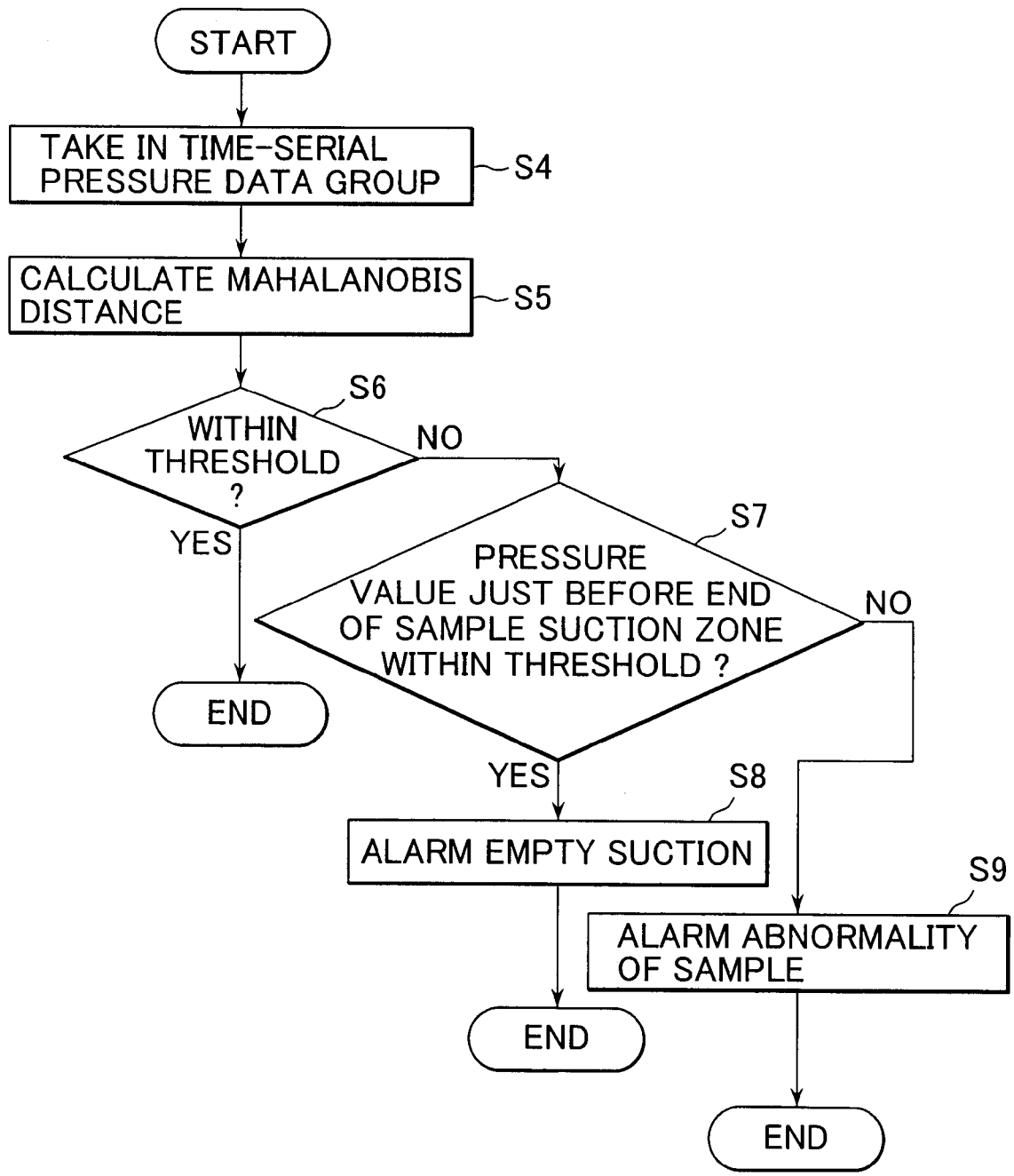
FIG. 12 is a control flowchart for discriminating plural types of abnormal dispensing in the present invention.

The abnormal dispensing occurs in various forms such as the complete clogging, the small clot suction, the highly viscous sample suction, and the empty suction, and the waveform of the pressure fluctuations changes depending on the various abnormal cases as shown in FIGS. 2A to 2I. Looking more closely, however, the empty suction differs from the other abnormal cases in that, upon the occurrence of an abnormality, the pressure is changed toward the positive pressure side relative to the normal waveform. By utilizing such a feature, when an abnormality is determined, it is possible to discriminate whether the occurred abnormality is generated by the empty suction or any other cause. FIG. 12 shows a control flow of the process for discriminating the empty suction.

Since discriminating the empty suction is also to detect one type of abnormal suction, the group of time-serial pressure data is taken in (S4), the Mahalanobis distance is calculated at that time (S5), and the calculated value is compared with the threshold (S6) as described above. When the compared result exceeds the threshold, this case is detected to be abnormal. If the abnormality is detected, the data immediately before the end of the sample suction zone is extracted from among the group of time-serial pressure data that has already been taken in, and then compared with a threshold (S7). In the case of empty suction, the pressure at the point of time immediately before the end of the sample suction zone is not deflected toward the negative pressure side. If the extracted data falls within a certain range of threshold, this case can be discriminated as the empty suction, and an alarm indicating the empty suction is issued (S8). If the extracted data exceeds the certain range of threshold, it is thought that this case represents a sample abnormality other than the empty suction, and an alarm indicating that fact is issued (S9).

The above-mentioned method utilizes the pressure value. As described above, the threshold determination using only a value is not robust against the output offset and gain variations of the pressure sensor, and increases a risk of false detection and missing of an abnormality. The influence of the output offset can be suppressed by calculating the difference from a value taken in before sucking the sample, but the gain cannot be compensated. However, because the direction in which the pressure deflects upon an abnormality is opposite with respect to the normal waveform between the empty suction and another type of dispensing abnormality, the threshold range used for discriminating them can be set to a relatively wide range. As a result, the empty suction can surely be discriminated from another type of dispensing abnormality.

Figure 13:
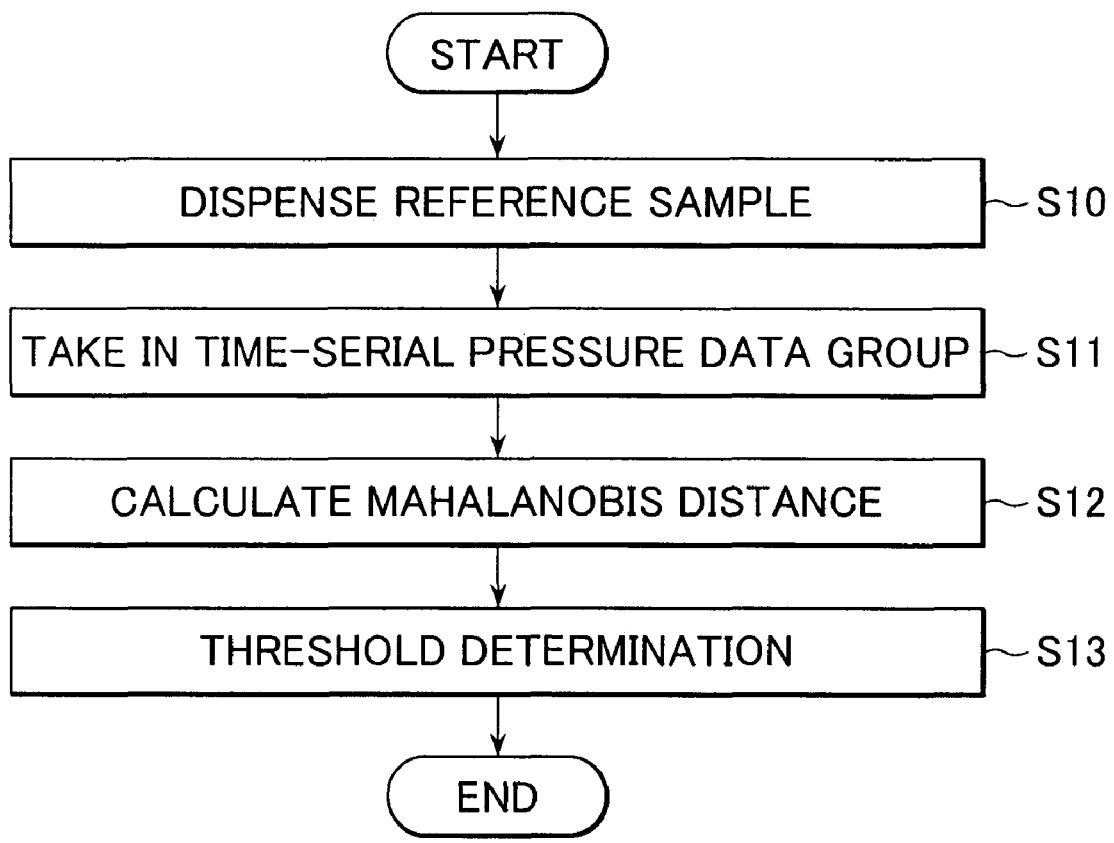
FIG. 13 is a control flowchart for checking an abnormality of a dispensing system in the present invention.

Utilizing the technique of the present invention makes it possible, in addition to the determination whether the dispensing is normally performed, to check an abnormality of the dispensing flow passage system, such as clogging of the sample probe, (hereinafter referred to as a "dispensing system abnormality check") by dispensing a normal sample as a reference (hereinafter referred to as a "reference sample") and looking at the waveform of the pressure fluctuations measured at that time. FIG. 13 shows a control flow for the dispensing system abnormality check.

As conditions required for the reference sample, it is important that individual differences of characteristics, such as viscosity and density, for each sample be hardly present, and that the sample can easily be prepared. Also, as a matter of course, the sample must not contain solid foreign matters, such as a clot. Examples of the reference sample satisfying those conditions include controlled serum and refined water. Alternatively, air is employed as the reference sample so that the empty suction is performed. Performing the empty suction is advantageous in that the necessity of preparing the reference sample is eliminated and there are no limiting conditions for the dispensing system abnormality check.

In a similar way to that described above, the reference sample is sucked (S10), the group of time-serial pressure data is taken in from the waveform of the pressure fluctuations at that time (S11), and the Mahalanobis distance is calculated (S12). The threshold determination is then made on a calculated value of the Mahalanobis distance (S13). If the calculated value exceeds the threshold, this can be regarded as indicating that any abnormality occurs in the dispensing flow passage system.

In the dispensing system abnormality check described above, whether the amount of the dispensed reference sample is large or small causes no problem so long as the presence or absence of an abnormality in the dispensing flow passage system can be detected. Accordingly, the check can be performed by deciding the amount of the dispensed reference sample to a certain value and dispensing the reference sample in the decided amount for each time. Stated another way, it is just required to decide one value of the amount of the dispensed reference sample and one type of the reference sample, and then to prepare one reference space for the dispensing system abnormality check.

The present invention is applicable to not only the check for detecting the presence or absence of clogging, but also to a check for detecting an abnormality of the pressure measuring system, e.g., a check for detecting a failure of the pressure sensor. By performing such a check each time the sample dispensing system is started up, therefore, the dispensing of a target sample can reliably be performed while confirming that any abnormality exists in neither the dispensing function nor the dispensing abnormality detecting function. Consequently, reliability of the dispensing can be increased.

Also, by performing the dispensing system abnormality check routinely once per day or week and recording checked results in a recorder, it is possible to predict the extent of deterioration of the apparatus in advance, and to utilize a predicted result for effective maintenance. For example, when the sample probe is repeatedly used, contaminants are attached to the opening end of the sample probe and gradually clog the probe opening. By predicting the progress of the clogging in advance, the contaminants can be removed or the sample probe can be replaced before the clogging cause a problem. Thus, reliable dispensing can be performed at all times.

Figure 14:
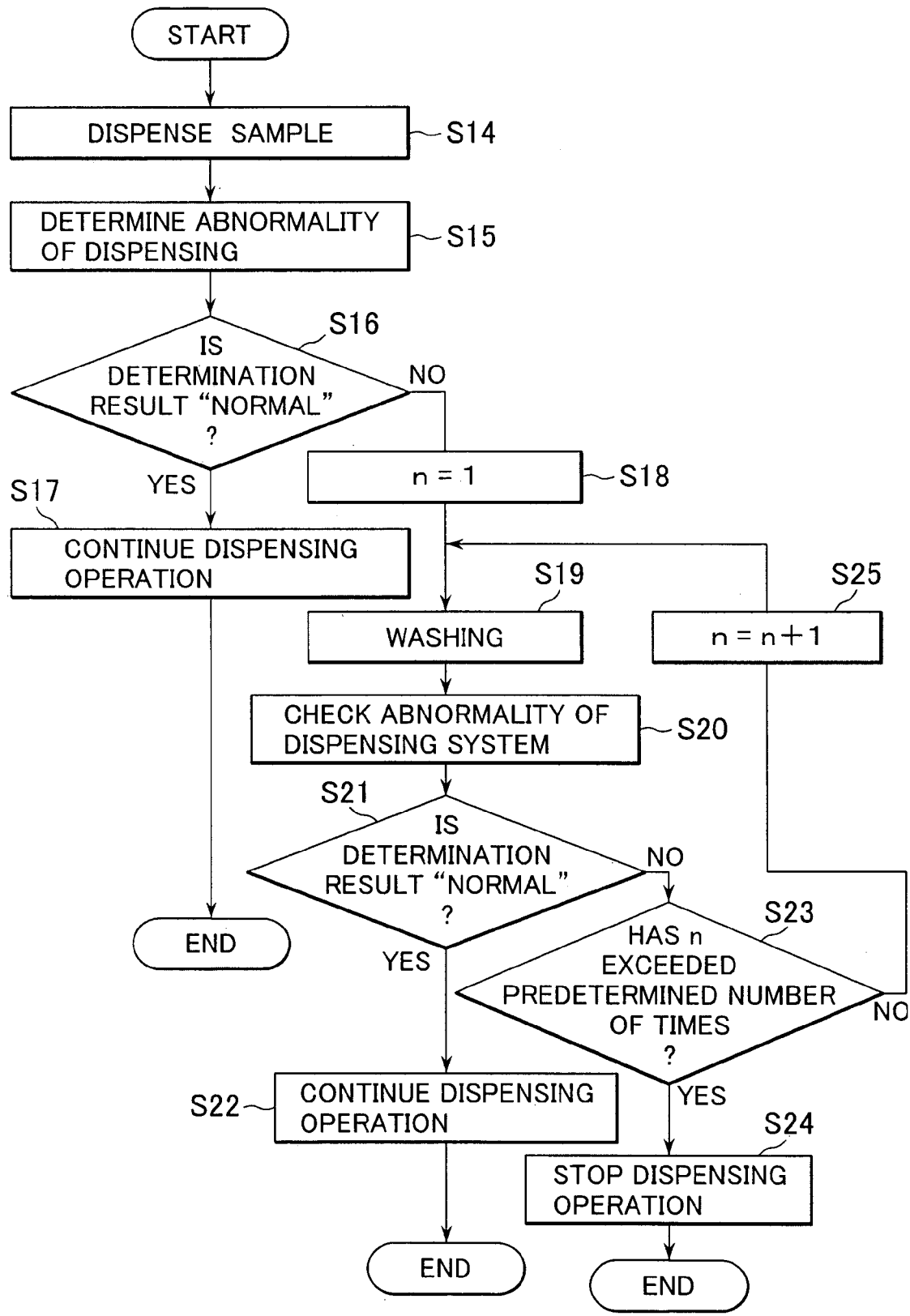
FIG. 14 is a control flowchart showing remedying operations performed subsequent to the occurrence of abnormal dispensing in the present invention.

Further, by utilizing the dispensing system abnormality check according to the present invention, when there occurs clogging during the sample dispensing, it is possible to wash out the clogging and to confirm whether the clogging has been removed with the washing. FIG. 14 shows a flowchart for such control.

After dispensing the sample (S14), whether the dispensing is normally performed is determined according to the present invention (S15). If a determination result is normal, the dispensing operation is continued (S17). If the determination result is abnormal, a washing action is performed, for example, by feeding cleaning water to the sample probe from the water supply pump, or by immersing the sample probe in a cleaning material, e.g., an acid or alkali (S19). After the end of the washing, a predetermined amount of the reference sample is dispensed to check whether the abnormality of the dispensing flow passage system, such as clogging, has been removed (S20). If a check result is normal, the dispensing operation is continued (S22). If the check result is abnormal, the washing and the dispensing system abnormality check are repeated again. The number of times at which the washing and the dispensing system abnormality check are repeated is counted (S25). If a counted value exceeds a predetermined number of times, this is regarded as indicating that the relevant abnormality is an abnormality which cannot be removed by the washing, and hence the dispensing operation is stopped (S24).

Note that the number of times at which the washing and the dispensing system abnormality check are repeated is not limited to a particular value. Alternatively, the number of times may be set to one so that the dispensing operation is stopped without repeating the washing.

Figure 15:
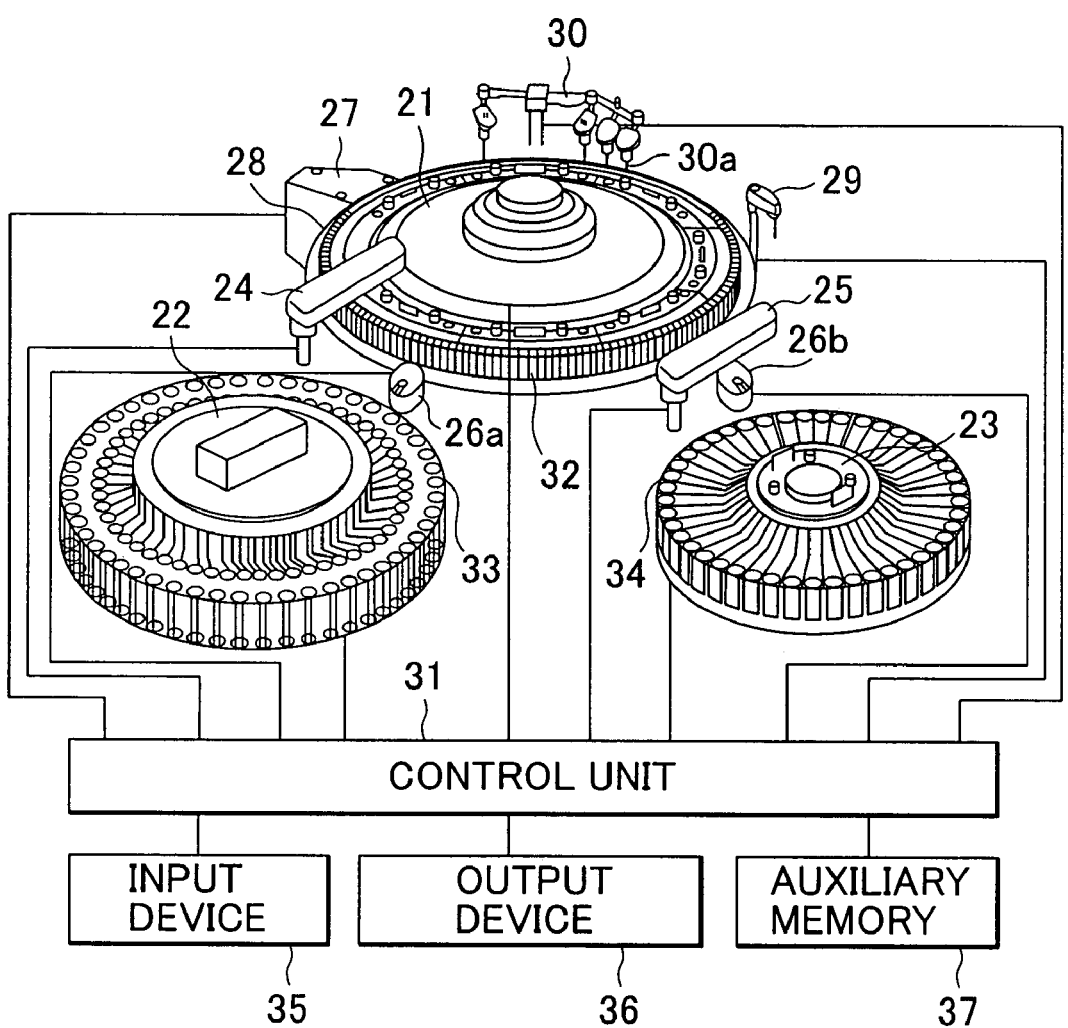
FIG. 15 schematically shows the construction of an automatic analyzer according to the present invention.

Next, a description is made of an embodiment in which the sample dispensing apparatus of the present invention is applied to an automatic analyzer. FIG. 15 schematically shows the construction of an automatic analyzer according to the present invention.

The automatic analyzer primarily comprises a reaction disk 21, a sample storing unit 22, a reagent storing unit 23, a sample dispensing apparatus 24, a reagent dispensing apparatus 25, cleaning baths 26a and 26b, a photometer 27, a reaction bath 28, an stirring mechanism 29, a cleaning mechanism 30, and a control unit 31. In the reaction disk 21, there are arranged a plurality of reaction vessels 32 for mixing and stirring a sample and a reagent. Also, a plurality of sample vessels 33 containing samples are arranged in the sample storing unit 22, and a plurality of reagent vessels 34 containing reagents are arranged in the reagent storing unit 23.

In addition to the components described above, the automatic analyzer of the present invention further comprises an input device 35, an output device 36, an auxiliary memory 37, etc. The control unit 31 supervises and controls the overall operation. With that configuration, an analysis item can be designated through the input device, and the analysis result and the presence or absence of dispensing abnormality can be displayed on the output device.

The automatic analyzer thus constructed carries out analysis through the following procedures. The reaction disk 21 including the plurality of reaction vessels 32 arranged thereon is rotated to move to a predetermined position, and a fixed amount of sample is dispensed from the sample storing unit 22 into the reaction vessel 32 by using the sample dispensing apparatus 24. Then, a fixed amount of reagent is dispensed from the reagent storing unit 23 into the reaction vessel 32, into which the sample has been just dispensed, by using the reagent dispensing apparatus 25. The reaction vessel 32, into which both the sample and the reagent have been dispensed, is rotated for transfer to the position of the stirring mechanism 29 for mixing and stirring. The sample and the reagent turn to a reaction liquid under the stirring and are transferred to the position of the photometer 27. The absorbance of the reaction liquid is measured for analysis of the sample. After the end of the analysis, the reaction vessel 32 is transferred to the position of the cleaning mechanism 30 in which the interior of the reaction vessel 32 is washed. Subsequently, a new sample and reagent are dispensed into the washed reaction vessel 32. Such a series of successive operations are repeatedly performed for each of the plurality of reaction vessels 32.

The automatic analyzer of this embodiment is featured in washing the reaction vessel 32, which has finished the analysis, by using the cleaning mechanism 30, and then employing the reaction vessel 32 repeatedly. The cleaning mechanism 30 has a plurality of cleaning nozzles 30a through which the reaction liquid is sucked, the cleaning material, e.g., an acid or alkali, is ejected and sucked, and the cleaning water is ejected and sucked. The automatic analyzer thus constructed accompanies with a problem that, when a sample including a clot is sucked by the sample dispensing apparatus 24 and the sample is ejected, as it is, into the reaction vessel 32, the clot is clogged in the cleaning nozzle 30a during the washing and the subsequent reaction vessels 32 can no longer be washed.

Figure 16:
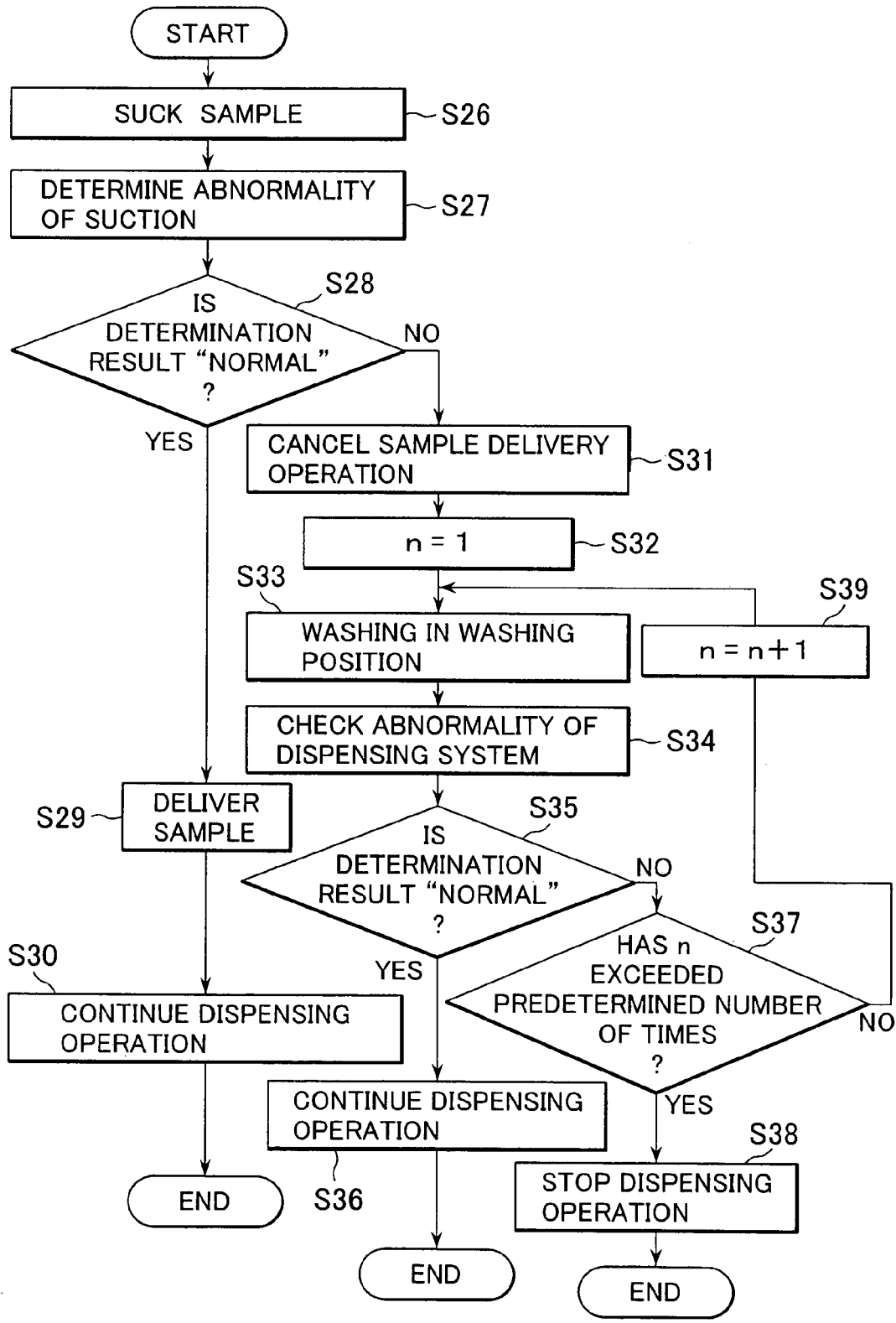
FIG. 16 is a control flowchart for discriminating plural types of abnormal dispensing in the present invention.

In view of the above problem, it is required in the sample dispensing apparatus that, when any abnormal sample is possibly sucked, the abnormal sample is prevented from being ejected into the reaction vessel. FIG. 16 shows a control flow for that purpose.

When a sample is sucked by the sample dispensing apparatus (S26), the group of time-serial pressure data is taken in with the sample suction zone being at the center, the Mahalanobis distance is calculated from the taken-in data group, and the threshold determination is made (S27). Those steps of processing are performed before the sample ejection, and it is determined based on the determination result whether the sucked sample is to be ejected into the reaction vessel. If it is determined that a normal sample has been sucked, the sample is ejected, as it is, into the reaction vessel (S29) and the subsequent dispensing operation is started (S30). If it is determined that an abnormal sample has been sucked, the operation of ejecting the sample into the reaction vessel is canceled (S31), and the sample dispensing apparatus is directly moved to the cleaning bath for washing (S33). It is desirable that, at the same time as canceling the operation of ejecting the sample into the reaction vessel, the other operations, such as the dispensing of a reagent and the stirring, which are to be performed for the relevant sample, be also canceled. This cancellation is advantageous in reducing a waste of the reagent. Thereafter, the sample dispensing apparatus is subjected to the dispensing system abnormality check (S34). Based on a check result, it is determined whether the dispensing operation is to be continued (S36) or stopped (S38).

Figure 17:
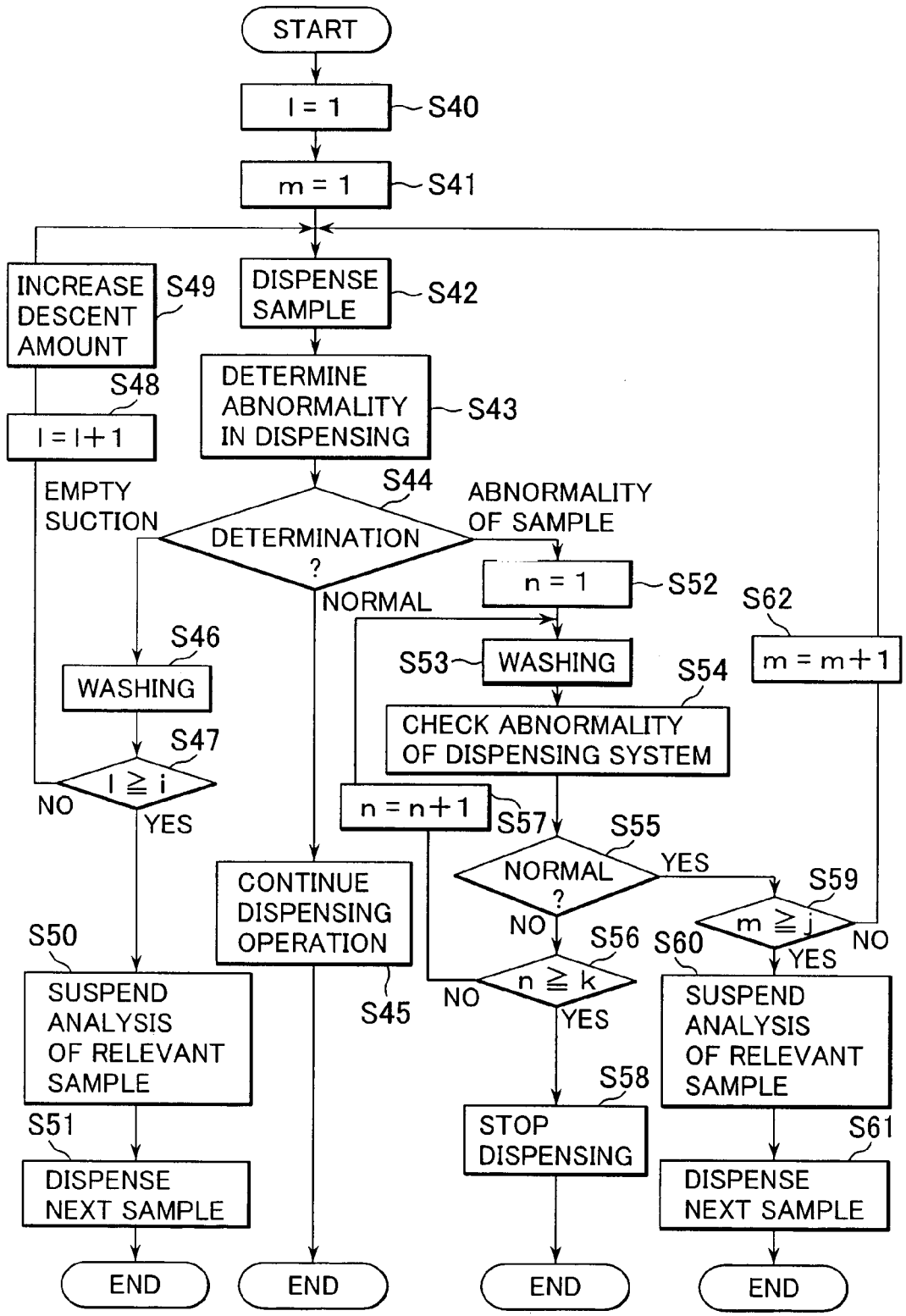
FIG. 17 is a control flowchart for discriminating plural types of abnormal dispensing in the present invention.

According to the present invention, it is possible not only to merely detect an abnormality during the dispensing, but also to determine whether the detected abnormality is caused by an abnormality of the sample or the empty suction. Therefore, the present invention enables a counteraction to be performed depending on the various different causes. FIG. 17 shows a control flow for that counteraction.

After dispensing a sample (S42), whether the dispensing has normally been performed is determined in accordance with the present invention (S43). If a determination result is normal, the subsequent dispensing operation is continued (S45).

If the empty suction is determined in the determination regarding the dispensing abnormality, the sample probe is washed (S46) and the dispensing operation is performed again on the same sample. Because the empty suction is possibly attributable to the fact that a descent amount of the sample probe is insufficient, the sample probe is descended in the next cycle of dispensing in a larger amount than that in the previous cycle of dispensing so as to enter the sample vessel to a larger extent (S49). While repeating similar processing in subsequent cycles of dispensing, the number of times of the empty suction is counted (S48). If the empty suction is continued in excess of a predetermined number of times, this is regarded as indicating that no sample is present in the sample vessel. Therefore, the analysis of the remaining analysis items for the relevant sample is canceled, and an alarm indicating the abnormality is displayed on the output device (S50). When the abnormality of dispensing is determined as empty suction, the sample dispensing apparatus is free from any abnormality, such as that the clogging of the sample probe cannot be removed. In other words, the dispensing can be continued without problems. Accordingly, even after the analysis of the relevant sample has been canceled, the operation proceeds to the dispensing of a next sample without stopping the automatic analyzer (S51).

Note that the number of times at which the dispensing is repeated for the same sample is not limited to a particular value. Alternatively, the number of times may be set to one so that the analysis of the relevant sample is canceled at once and the dispensing of a next sample is started.

If it is determined in the dispensing abnormality determination that the sample is abnormal, the sample probe is washed (S53). Thereafter, a reference sample is dispensed to carry out the dispensing system abnormality check (S54). If a check result is abnormal, the washing is repeated. If the abnormality is not removed even after repeating the washing, an operator must manually remove the abnormality. In this case, the sample dispensing apparatus stops the dispensing (S58), and an alarm indicating the abnormal condition is issued to the output device. Because the dispensing is no longer continued in this case unless the abnormality is removed, another auditory or visual alarm, such as an alarm sound or light, may also be issued.

If it is determined in the dispensing abnormality determination that the sample is abnormal, but the clogging is removed after the washing and the dispensing system abnormality check shows no problems, the dispensing is performed again on the same sample. If the sample abnormality is continued in excess of a predetermined number of times while the dispensing is repeated on the same sample, this is regarded as indicating that the relevant sample includes many clots. Therefore, the analysis of the remaining analysis items for the relevant sample is canceled, and an alarm indicating the abnormality is displayed on the output device (S60). However, the cancellation is made only for the relevant sample, and the operation proceeds to the dispensing of a next sample without stopping the automatic analyzer (S61).

According to the present invention, since various types of abnormal dispensing causing analysis failures can be all detected regardless of the type and extent of abnormality, reliability of the sample dispensing apparatus and analysis results of the automatic analyzer employing the sample dispensing apparatus can be increased. Consequently, the present invention is also effective in reducing labor and cost required for management of samples in an inspection room.

Further, the method of determining an abnormality of dispensing according to the present invention has sufficient robustness against variations of sensitivity of the pressure sensor, and is able to accurately detect the abnormality of dispensing without reducing the detection ability with no need of performing close adjustment or narrowing working tolerances. As a result, it is possible to suppress the cost that is otherwise expected to increase due to the necessity of those additional steps.

In addition, according to the present invention, when there occurs a dispensing abnormality, the subsequent actions for dealing with the abnormality can be automatically performed, and therefore the processing efficiency can be increased. Also, in the event of an abnormality, whether the abnormality has been removed can be detected with high accuracy, and hence higher reliability is ensured.

What is claimed is:

1. A sample dispensing apparatus comprising a probe for sucking and ejecting a sample, a dispensing syringe for generating a pressure in said probe to suck and eject the sample, a dispensing flow passage connecting said probe and said dispensing syringe, and a control unit for controlling sucking and ejection operations of the sample, the apparatus further comprising:
   at least one pressure sensor for detecting a pressure in said dispensing flow passage;
   pressure value storing means for time-serially storing output values of said pressure sensor during an operation of dispensing the sample;
   storage means for storing a reference database consisted of time-serial output values of said pressure sensor, which are obtained when the sample is normally sucked or ejected by said probe; and
   determining means for determining an abnormality of sample dispensing by comparing the Mahalanobis distance calculated from both comparison data prepared based on the output values of said pressure sensor time-serially stored in said pressure value storing means and said reference database, with a preset threshold.

2. A sample dispensing apparatus according to claim 1, wherein said reference database is prepared depending on an amount of dispensed sample, and the abnormality of sample dispensing is determined by comparing the Mahalanobis distance calculated from both said comparison data and reference database corresponding to the amount of dispensed sample, with a preset threshold.

3. A sample dispensing apparatus according to claim 1, comprising:
discriminating means for, when the abnormality of sample dispensing is detected, comparing a pressure value immediately before the end of the sample sucking operation with a preset threshold, and for discriminating a cause of the dispensing abnormality.

4. An automatic analyzer including a sample dispensing apparatus according to claim 3,
wherein said automatic analyzer has a function of, when an abnormality of sample dispensing is detected, finding out a cause of the dispensing abnormality from among a plurality of classified causes and displaying the found-out cause.

5. An automatic analyzer including a sample dispensing apparatus according to claim 4,
wherein said automatic analyzer has a function of displaying the cause of the dispensing abnormality and performing a counteraction corresponding to the cause.

6. A sample dispensing apparatus according to claim 1,
wherein the determining means includes dispensing-function abnormality determining means for, when a fluid having a known physical property falling within a predetermined range of said physical property for samples handled by said sample dispensing apparatus, is dispensed as the sample, determining the abnormality of dispensing and determining the presence or absence of an abnormality in a dispensing function of said sample dispensing apparatus, by reference to said time-serial output values of said reference database, stored for a reference sample having the known physical property falling within said predetermined range.

7. A sample dispensing apparatus according to claim 6,
wherein said sample dispensing apparatus has a function of determining the abnormality of dispensing each time said sample dispensing apparatus is started up, and determining the presence or absence of the abnormality in the dispensing function of said sample dispensing apparatus.

8. A sample dispensing apparatus according to claim 6,
wherein the determining means includes recording means for routinely determining the abnormality of dispensing and time-serially recording determination results, and means for discriminating the extent of deterioration in the dispensing function of said sample dispensing apparatus.

9. A sample dispensing apparatus according to claim 1, further comprising:
cleaning means for washing the interior of said dispensing flow passage including said sample probe; and
wherein said sample dispensing apparatus has a function of, when the abnormality of sample dispensing is detected, washing the interior of said dispensing flow passage including said sample probe, then dispensing a fluid having a known physical property falling within a predetermined range of said physical property for samples handled by said sample dispensing apparatus, and determining the dispensing abnormality in the fluid dispensing by reference to said time-serial output values of said reference database, stored for a reference sample having the known physical property falling within said predetermined range, thereby determining whether the dispensing function of said sample dispensing apparatus is restored.

10. A sample dispensing apparatus comprising a probe for sucking and ejecting a sample, a dispensing syringe for generating a pressure in said probe to suck and eject the sample, a dispensing flow passage connecting said probe and said dispensing syringe, and a control unit for controlling sucking and ejection operations of the sample, said apparatus further comprising:
at least one pressure sensor for detecting a pressure in said dispensing flow passage;
pressure value storing means for time-serially storing output values of said pressure sensor during an operation of dispensing the sample;
storage means for storing a reference database consisted of time-serial output values of said pressure sensor, which are obtained when the sample is normally sucked or ejected by said probe;
determining means for carrying out multi-variable analysis of both said reference database and comparison data created based on the output values of said pressure sensor time-serially stored in said pressure value storing means, and for determining the presence or absence of an abnormality in the dispensing operation of the sample based on an analysis result; and
cleaning means for washing the interior of said dispensing flow passage including said sample probe;
wherein said sample dispensing apparatus has a function of, when the abnormality of sample dispensing is detected, washing the interior of said dispensing flow passage including said sample probe, then dispensing a fluid having a known physical property falling within a predetermined range of said physical property for samples handled by said sample dispensing apparatus, and determining the dispensing abnormality in the fluid dispensing by reference to said time-serial output values of said reference database, stored for a reference sample having the known physical property falling within said predetermined range, thereby determining whether the dispensing function of said sample dispensing apparatus is restored.

11. A sample dispensing apparatus according to claim 10.
wherein said sample dispensing apparatus has a function of stopping the dispensing operation when the abnormality of sample dispensing is detected and thereafter the dispensing function of said sample dispensing apparatus is not restored even after repeating the washing a predetermined number of times.

12. An automatic analyzer including a sample dispensing apparatus, comprising a probe for sucking and ejecting a sample, a dispensing syringe for generating a pressure in said probe to suck and eject the sample, a dispensing flow passage connecting said probe and said dispensing syringe, and a control unit for controlling sucking and ejection operations of the sample, said apparatus further comprising:
at least one pressure sensor for detecting a pressure in said dispensing flow passage;
pressure value storing means for time-serially storing output values of said pressure sensor during an operation of dispensing the sample;
storage means for storing a reference database consisted of time-serial output values of said pressure sensor, which are obtained when the sample is normally sucked or ejected by said probe;
determining means for carrying out multi-variable analysis of both said reference database and comparison data created based on the output values of said pressure sensor time-serially stored in said pressure value storing means, and for determining the presence or absence of an abnormality in the dispensing operation of the sample based on an analysis result; and a cleaning bath for cleaning an outer surface of a sample probe, a reaction vessel cleaning mechanism, and a reaction vessel repeatedly used after being washed by said reaction vessel cleaning mechanism, wherein said automatic analyzer has a function of, when an abnormality of dispensing is detected during suction of a sample, discarding the sample into said cleaning bath without ejecting the sample into said reaction vessel.

13. An automatic analyzer including:

a sample dispensing apparatus comprising a probe for sucking and ejecting a sample, a dispensing syringe for generating a pressure in said probe to suck and elect the sample, a dispensing flow passage connecting said probe and said dispensing syringe, and a control unit for controlling sucking and ejection operations of the sample, said apparatus further comprising:

at least one pressure sensor for detecting a pressure in said dispensing flow passage;

pressure value storing means for time-serially storing output values of said pressure sensor during an operation of dispensing the sample;

storage means for storing a reference database consisted of time-serial output values of said pressure sensor, which are obtained when the sample is normally sucked or ejected by said probe; and determining means for carrying out multi-variable analysis of both said reference database and comparison data created based on the output values of said pressure sensor time-serially stored in said pressure value storing means, and for determining the presence or absence of an abnormality in the dispensing operation of the sample based on an analysis result;

wherein the determining means includes discriminating means for, when the abnormality of sample dispensing is detected, comparing a pressure value immediately before the end of the sample sucking operation with a preset threshold, and for discriminating a cause of the dispensing abnormality, and wherein said automatic analyzer has a function of, when an abnormality of sample dispensing is detected, finding out a cause of the dispensing abnormality from among a plurality of classified causes and displaying the found-out cause.

14. An automatic analyzer according to claim 13, wherein said automatic analyzer has a function of displaying the cause of the dispensing abnormality and performing a counteraction corresponding to the cause.

15. An automatic analyzer including a sample dispensing apparatus, comprising a probe for sucking and ejecting a sample, a dispensing syringe for generating a pressure in said probe to suck and eject the sample, a dispensing flow passage connecting said probe and said dispensing syringe, and a control unit for controlling sucking and ejection operations of the sample, said apparatus further comprising:

at least one pressure sensor for detecting a pressure in said dispensing flow passage;

pressure value storing means for time-serially storing output values of said pressure sensor during an operation of dispensing the sample;

storage means for storing a reference database consisted of time-serial output values of said pressure sensor, which are obtained when the sample is normally sucked or ejected by said probe; and determining means for carrying out multi-variable analysis of both said reference database and comparison data created based on the output values of said pressure sensor time-serially stored in said pressure value storing means, and for determining the presence or absence of an abnormality in the dispensing operation of the sample based on an analysis result;

wherein said automatic analyzer has a function of, when an abnormality of sample dispensing is detected, repeatedly dispensing the relevant sample within a predetermined number of times.

16. An automatic analyzer including a sample dispensing apparatus, comprising a probe for sucking and ejecting a sample, a dispensing syringe for generating a pressure in said probe to suck and eject the sample, a dispensing flow passage connecting said probe and said dispensing syringe, and a control unit for controlling sucking and ejection operations of the sample, said apparatus further comprising:

at least one pressure sensor for detecting a pressure in said dispensing flow passage;

pressure value storing means for time-serially storing output values of said pressure sensor during an operation of dispensing the sample;

storage means for storing a reference database consisted of time-serial output values of said pressure sensor, which are obtained when the sample is normally sucked or ejected by said probe; and determining means for carrying out multi-variable analysis of both said reference database and comparison data created based on the output values of said pressure sensor time-serially stored in said pressure value storing means, and for determining the presence or absence of an abnormality in the dispensing operation of the sample based on an analysis result;

wherein said automatic analyzer has a function of, when an abnormality of sample dispensing is detected and then the dispensing abnormality still continues even after repeatedly dispensing the relevant sample within a predetermined number of times, canceling the dispensing of the relevant sample and starting to dispense a next sample.

17. A method of detecting an abnormality during sample dispensing, comprising the steps of:

sucking a sample by using a probe;

time-serially storing output values of a pressure sensor representing pressures in said probe and detected during said sucking step;

creating comparison data based on the stored output values of said pressure sensor; and determining an abnormality of sample dispensing by comparing the Mahalanobis distance calculated from both the comparison data and a reference database consisting of the time-serial output values of said pressure sensor, which are obtained when the sample is normally sucked or ejected by said probe, with a preset threshold.

* * * * *

UNITED STATES PATENT AND TRADEMARK OFFICE
CERTIFICATE OF CORRECTION

| | |
|---|---|
| PATENT NO. | : 7,027,935 B2 |
| APPLICATION NO. | : 10/634775 |
| DATED | : April 11, 2006 |
| INVENTOR(S) | : Akihiro Shimase et al. |

Page 1 of 1

It is certified that error appears in the above-identified patent and that said Letters Patent is hereby corrected as shown below:

Title page, Item [73],

Please correct the error in the Assignee from "Hitachi High Technologies Corp." to --Hitachi High-Technologies Corp.--

Signed and Sealed this

Twelfth Day of December, 2006

JON W. DUDAS
*Director of the United States Patent and Trademark Office*